US008340746B2

(12) United States Patent
Syed et al.

(10) Patent No.: US 8,340,746 B2
(45) Date of Patent: Dec. 25, 2012

(54) MOTIF DISCOVERY IN PHYSIOLOGICAL DATASETS: A METHODOLOGY FOR INFERRING PREDICTIVE ELEMENTS

(75) Inventors: Zeeshan H. Syed, Wayzata, MN (US); John V. Guttag, Lexington, MA (US); Collin M. Stultz, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 498 days.

(21) Appl. No.: 12/504,529

(22) Filed: Jul. 16, 2009

(65) Prior Publication Data
US 2010/0016748 A1 Jan. 21, 2010

Related U.S. Application Data

(60) Provisional application No. 61/081,437, filed on Jul. 17, 2008, provisional application No. 61/081,445, filed on Jul. 17, 2008.

(51) Int. Cl.
*A61B 5/04* (2006.01)
(52) U.S. Cl. ...................................... 600/509
(58) Field of Classification Search ............... 600/509, 600/513, 515–519; 607/17, 18
See application file for complete search history.

(56) References Cited

U.S. PATENT DOCUMENTS

| 7,031,765 | B2 | 4/2006 | Ritscher et al. |
| 7,069,070 | B2 | 6/2006 | Carlson et al. |
| 7,599,733 | B1 * | 10/2009 | Wirasinghe et al. ......... 600/510 |
| 7,949,389 | B2 | 5/2011 | Wolfberg et al. |
| 2001/0034488 | A1 * | 10/2001 | Policker et al. ............... 600/515 |
| 2002/0103512 | A1 | 8/2002 | Echauz et al. |
| 2003/0204146 | A1 | 10/2003 | Carlson |
| 2004/0068199 | A1 | 4/2004 | Echauz et al. |
| 2004/0147815 | A1 | 7/2004 | Skinner |
| 2004/0176696 | A1 | 9/2004 | Mortara |
| 2005/0010124 | A1 | 1/2005 | Couderc et al. |
| 2005/0085734 | A1 | 4/2005 | Tehrani |
| 2006/0056655 | A1 | 3/2006 | Wen et al. |
| 2008/0097537 | A1 * | 4/2008 | Duann et al. .................... 607/14 |
| 2009/0192394 | A1 | 7/2009 | Guttag et al. |

FOREIGN PATENT DOCUMENTS

WO 9406350 3/1994

(Continued)

OTHER PUBLICATIONS

Tuzcu et al., "Dynamic Time Warping As a Novel Tool in Pattern Recognition of ECG Changes in Heart Rhythm Disturbances," Systems, Man and Cybernetics, 2005 IEEE International Conference on, IEEE, Piscataway, NJ, USA, vol. 1, Oct. 10, 2005, pp. 182-186.

(Continued)

*Primary Examiner* — Brian T Gedeon
(74) *Attorney, Agent, or Firm* — K&L Gates LLP

(57) ABSTRACT

The application relates a methodology and apparatus for identifying predictive patterns for acute clinical events in the absence of prior knowledge. Principles of conservation are used to identify activity that consistently precedes an outcome in patients, and describe a two-stage process that allows us to more efficiently search for such patterns in large datasets. This is achieved by first transforming continuous physiological signals from multiple patients into symbolic sequences, and by then searching for patterns in these reduced representations that are strongly associated with an outcome.

25 Claims, 13 Drawing Sheets

Continuous ECG Waveform

Symbolic Representation

αβγδαβγδαβγδαβγδ

FOREIGN PATENT DOCUMENTS

WO             0010455         3/2000

OTHER PUBLICATIONS

Vullings et al., "Automated ECG segmentation with Dynamic Time Warping," Engineering in Medicine and biology Society, 1998, Proceedings of the 20th Annual International Conference of the IEEE Hong Kong, China Oct. 29-Nov. 1, 1998, Piscataway, NJ, USA, IEE, US, pp. 163-166.

Vyklicky et al., "Analysis of dynamic changes in ECG Signals during Optical Mapping by Dynamic Time Warping," Computers in Cardiology, 2005, Lyon, France, Sep. 25-28, 2005, Piscataway, NJ, USA, IEEE, Sep. 25, 2005, pp. 543-546.

International Search Report and Written Opinion of the International Searching Authority for International Application No. PCT/US2009/000279, mailed Apr. 15, 2009 (19 pgs.).

Syed et al., "ECG Markers to Predict Cardiovascular Death: Heart Rate Variability, Deceleration Capacity and Morphologic Variability in Non-ST-Elevation ACS from the Merlin TIMI-36 Trial," American Heart Association Scientific Sessions, New Orleans, LA, Nov. 14-18, 2008.

Syed et al., "Morphologic Variability: A new Elecrocardiographic Technique for Risk Stratification After NSTEACS," American Heart Association Scientific Sessions, Orlando, FL, Nov. 4-7, 2007.

\* cited by examiner

Continuous ECG Waveform

Symbolic Representation

αβγδαβγδαβγδαβγδα

MOTIF DISCOVERY IN PHYSIOLOGICAL DATASETS: A METHODOLOGY FOR INFERRING PREDICTIVE ELEMENTS

CROSS-REFERENCE TO RELATED APPLICATION

This application claims priority to and the benefit of U.S. Provisional Patent Application No. 61/081,437, filed Jul. 17, 2008, and U.S. Provisional Patent Application No. 61/081,445, filed Jul. 17, 2008, the entire disclosures of each of which are hereby incorporated by reference herein.

BACKGROUND

An extensive literature exists in the area of machine learning on the subject of prediction. A common approach is to infer prediction rules from the data of the form:

IF $cond_1$ AND ... $cond_i$ ... AND $cond_m$ THEN pred

These rules correspond to a set of conditions associated with a specific outcome. The challenge is to select conditions that are able to distinguish between whether an event occurs or not, but do not overfit available training data. A number of different techniques exist for this purpose, ranging from decision trees. However, current techniques are typically insufficient for discovering potentially predictive activity preceding acute events.

SUMMARY OF THE INVENTION

The invention relates to a methodology and apparatus for identifying predictive patterns for acute clinical events in the absence of prior knowledge. We use the principle of conservation to identify activity that consistently precedes an outcome in patients, and describe a two-stage process that allows us to more efficiently search for such patterns in large datasets. This is achieved by first transforming continuous physiological signals from multiple patients into symbolic sequences, and by then searching for patterns in these reduced representations that are strongly associated with an outcome.

We focus on identifying conserved activity that is unlikely to have occurred purely by chance in all patients who experienced an event. This strategy of finding statistically significant conserved patterns in symbolic sequences is analogous to the discovery of regulatory motifs in genomic datasets. We build upon existing work in the area of computational biology to discover conserved patterns within a group of strings, generalizing the notion of a regulatory motif and enhancing current techniques to operate robustly on symbols that have been derived from a broad set of signals, including physiological data. Physiological data includes, for example, electrophysiological data. This allows us to develop a framework for information inference, where we can identify precursors as activity that has a high probability of occurring preceding an event. This activity may not always occur in precisely the same form, i.e., it may be approximately conserved, with small variations. Moreover, we do not make any assumptions about the nature of this activity, and allow it to be of arbitrary complexity.

We describe the domain-specific challenges associated with a general-purpose, unsupervised inference methodology similar to the one proposed and detail the benefits and limitations of modeling the problem of discovering predictive elements in a regulatory, motif-discovery setting. Our work also attempts to address two significant considerations associated with motif discovery in general, i.e., computational efficiency and robustness in the presence of degeneracy and noise. To deal with these issues, we identify active regions in each symbolic signal that are likely to contain regulatory activity and should be analyzed more closely, and propose new subset-based techniques, such as a two-layer Gibbs sampling algorithm, which are able to handle noise by excluding outliers where predictive patterns may be absent or increasingly degenerate.

We evaluated our solution on a population of patients who experienced sudden cardiac death and attempt to discover electrocardiographic activity that may be associated with the endpoint of death. To assess the predictive patterns discovered, we compared the scores for the sudden death population against control populations of normal individuals and those with non-fatal supraventricular arrhythmias. Our results suggest that predictive motif discovery may be able to identify clinically relevant information even in the absence of significant prior knowledge.

The subject of finding predictive elements has been extensively studied in a wide variety of contexts including geodesic, medical and financial data. In this application, we present a motif discovery methodology for discovering precursors. While we focus mainly on physiological datasets, we present general techniques that may be broadly applicable to a wider group of signals.

We model prediction as the problem of identifying activity that consistently precedes an event of interest. In the absence of any prior knowledge, this activity can be discovered by observing multiple occurrences of the event and detecting statistically significant commonalities in the data preceding it, i.e., by searching for conserved elements unlikely to occur purely by chance prior to the event of interest (FIG. 1). To handle noise, we further adopt a relaxed view of conservation, whereby precursors may approximately match or be altogether absent on some observations of the event. A further practical consideration is that the search be computationally efficient to handle large amounts of data resulting from multiple observations.

This model of prediction is similar to the search for regulatory motifs in the setting of computational biology. Motif discovery techniques operate on genomic datasets and search for DNA sequences that are conserved across genomes. We generalize this model and describe how the search for precursors to acute clinical events can be carried out in an analogous manner, by first converting continuous physiological signals into an alphabetical representation, and then mining this representation for conserved activity. A variety of randomized greedy algorithms can be used to efficiently carry out the search for such patterns. We use techniques such as TCM and Gibbs sampling as the foundation of our work, and enhance them to operate on data with highly divergent background distributions of symbols, frequent noise and patterns of increased degeneracy relative to genomic data.

The rest of this application describes the proposed unsupervised inference methodology. While the techniques we suggest can be used on a variety of signals and are sufficiently general-purpose, we motivate them in the more concrete setting of searching for predictive activity in physiological signals. We detail the challenges associated with such an approach and describe its benefits and limitations.

Section 2 details the concept and challenges of representing continuous physiological signals as symbolic strings. The subsequent section 3 presents a similar discussion of the problem of detecting predictive motifs in string data. The next following section 4 describes existing computational biology algorithms for motif detection, while the $5^{th}$ section proposes data transformations and algorithms (including a two-level Gibbs sampling technique) that have been augmented to search for motifs in a computationally-efficient manner in the presence of noise and degeneracy. An application of our work to sudden cardiac death data is discussed in section 6. Related work is presented in section 7. This is followed by a discussion of morphologic entropy in section 8, and an evaluation of this method in section 9. Finally, a summary and conclusions appear in the last section.

In one aspect, the invention relates to a method of detecting patterns in a physiological signal. The method includes the steps of recording a physiological signal from a patient; segmenting the physiological signal into a plurality of components; grouping the components into a plurality of information classes; assigning a representation to each information class; and searching for patterns of these representations. In some embodiments, the representation is a numerical value, and in some embodiments, the representation is a symbol. In some embodiments the representation is a waveform, such as, for example, a prototype (archetype) waveform or a centrotype waveform.

In some embodiments, the pattern may be predictive. In some embodiments, the pattern may be a sequence of representations. In some embodiments, the sequence of representations occurs more often than expected given the distribution of symbols. In some embodiments, the pattern can be a sequence of representations that occur more often than expected in patients who have an event, or the pattern can be a sequence of representations that occur more often than expected in patients who have an event relative to patients who do not have an event. In some embodiments, the pattern may be the entropy of the representations. In some embodiments, the method includes the further step of compressing multiple equivalent time portions that contain normal (e.g., uninteresting and/or unremarkable) physiological signals. In some embodiments, the method includes the further step of removing multiple equivalent time portions that contain normal physiological signals. In some embodiments, the method includes the further step of assigning a significant event to a predictive substantially conserved sequence of symbols. In some embodiments, the physiological signal is an ECG and the an equivalent time portion is a heartbeat.

In one aspect, the invention relates to an apparatus for detecting patterns in a physiological signal. The apparatus includes a computer having a module for dividing the physiological signal into a plurality of equivalent time portions; and a module for assigning a symbol to each portion of the plurality of equivalent time portions. In some embodiments, the apparatus can further include a module for recording the physiological signal from a patient. In some embodiments, the apparatus can further include a module for removing multiple equivalent time portions which comprise normal physiological signals. In some embodiments, the apparatus can further include a module for compressing multiple equivalent time portions which comprise normal physiological signals. In some embodiments, the apparatus can further include a module for assigning a significant event to a predictive substantially conserved sequence of symbols. In some embodiments, the module for recording a physiological signal is an ECG and the equivalent time portion is a heartbeat.

In one aspect, the invention relates to a method of detecting patterns in an electrocardiogram. The method includes the steps of recording an electrocardiogram from a patient; dividing the electrocardiogram into a plurality of heartbeats; and assigning a symbol to each heartbeat of the plurality of heartbeats. In some embodiments, the method can include the further step of assigning a significant event to a predictive substantially conserved sequence of symbols.

In one aspect, the invention relates to a method of finding a consensus motif of length W in a set of physiological data sequences $S=\{S_i, \ldots, S_n\}$ utilizing a working set $V=\{v_i, \ldots, v_c\}$. The method includes the steps of (a) obtaining the physiological data set (S); (b) estimating a profile matrix M for the working set $\{V-v_i\}$ wherein V is an initial subset of set S and $v_i$ member of the working set V; (c) calculating a probability that a member $v_i$ of the working set V will be swapped out; (d) if the probability that $v_i$ is swapped out exceeds a predetermined probability $p_{pd}$, then swap out $v_i$ for $v_{inew}$; and disable swap of $v_{inew}$ for k iterations; (e) select new initial staring position $p_{new}$; and (f) repeat until M is less than some threshold $\epsilon$. In some embodiments, the method includes the further steps of (1) choosing an initial subset V of set S; (2) selecting an initial starting position p; and (3) selecting a member $v_i$ of the working set V, prior to estimating the profile matrix M. In some embodiments, the initial starting position is selected randomly. In some embodiments, the probability that $v_i$ is swapped out is a probability function, and in some embodiments the probability function is a function of maximum score. In some embodiments, the selecting of a new initial staring position $p_{new}$ is random.

In one aspect, the invention relates to a method of finding a consensus motif of length W in a set of physiological data sequences $S=\{S_i, \ldots, S_n\}$ utilizing a working set $V=\{v_i, \ldots, v_c\}$. The method includes the steps of (a) obtaining physiological data set S; (b) choosing an initial subset V of set S; (c) selecting an initial starting position p; (d) selecting a member $v_i$ of the working set V; (e) estimating a profile matrix M for the working set $\{V-v_i\}$; (f) calculating a probability that a member $v_i$ of the working set V will be swapped out; (g) if the probability that $v_i$ is swapped out exceeds a predetermined probability $p_{pd}$, then swap out $v_i$ for $v_{inew}$; and disable swap of $v_{inew}$ for k iterations; (h) select new initial staring position $p_{new}$; and (i) repeat steps c-g until M is less than some threshold $\epsilon$.

In one aspect, the invention relates to a method of detecting patterns in an electrocardiogram. The method includes the steps of recording an electrocardiogram from a patient; dividing the electrocardiogram into a plurality of heartbeats; and assigning a symbol to each heartbeat of the plurality of heartbeats. In some embodiments, the method can include the further step of assigning a significant event to a predictive substantially conserved sequence of symbols.

BRIEF DESCRIPTION OF THE DRAWINGS

The aspects, embodiments, and features of the invention can be better understood with reference to the drawings described herein. The drawings are provided to highlight specific embodiments of the invention and are not intended to limit the invention, the scope of which is defined by the claims.

DESCRIPTION OF A PREFERRED EMBODIMENT

These and other aspects, embodiments, and features of the invention are further described in the following sections of the application, which are provided to highlight specific embodiments of the invention and are not intended to limit the invention. Other embodiments are possible and modifications may be made without departing from the spirit and scope of the invention. In addition, the use of sections in the application is not meant to limit the invention; each section can apply to any aspect, embodiment, or feature of the invention.

It should be understood that the order of the steps of the methods of the invention is immaterial so long as the invention remains operable. Moreover, two or more steps may be conducted simultaneously or in a different order than recited herein unless otherwise specified.

Section 2: Symbolic Representation of Physiological Data

The notion of representing physiological signals as symbolic sequences follows from the quasi-periodic nature of many important signals. For example, data from the heart and lungs often comprises units such as heart beats or breaths, which are repetitive. It is often more natural to analyze physiological signals in terms of these units than at the level of raw samples.

Figure 1:
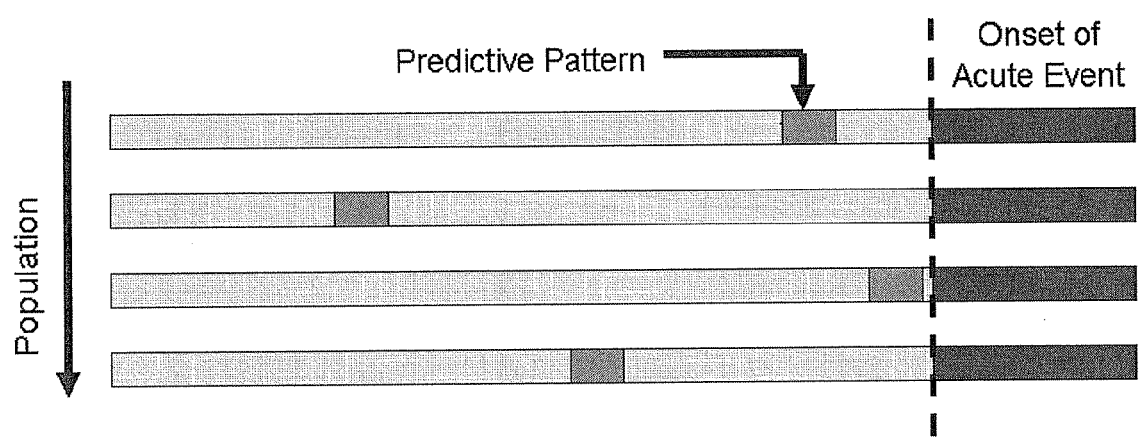
FIG. 1 shows a prediction through conservation in the context of a population of patients affected by a common acute clinical event, in accordance with an illustrative embodiment of the invention.
Figure 2:
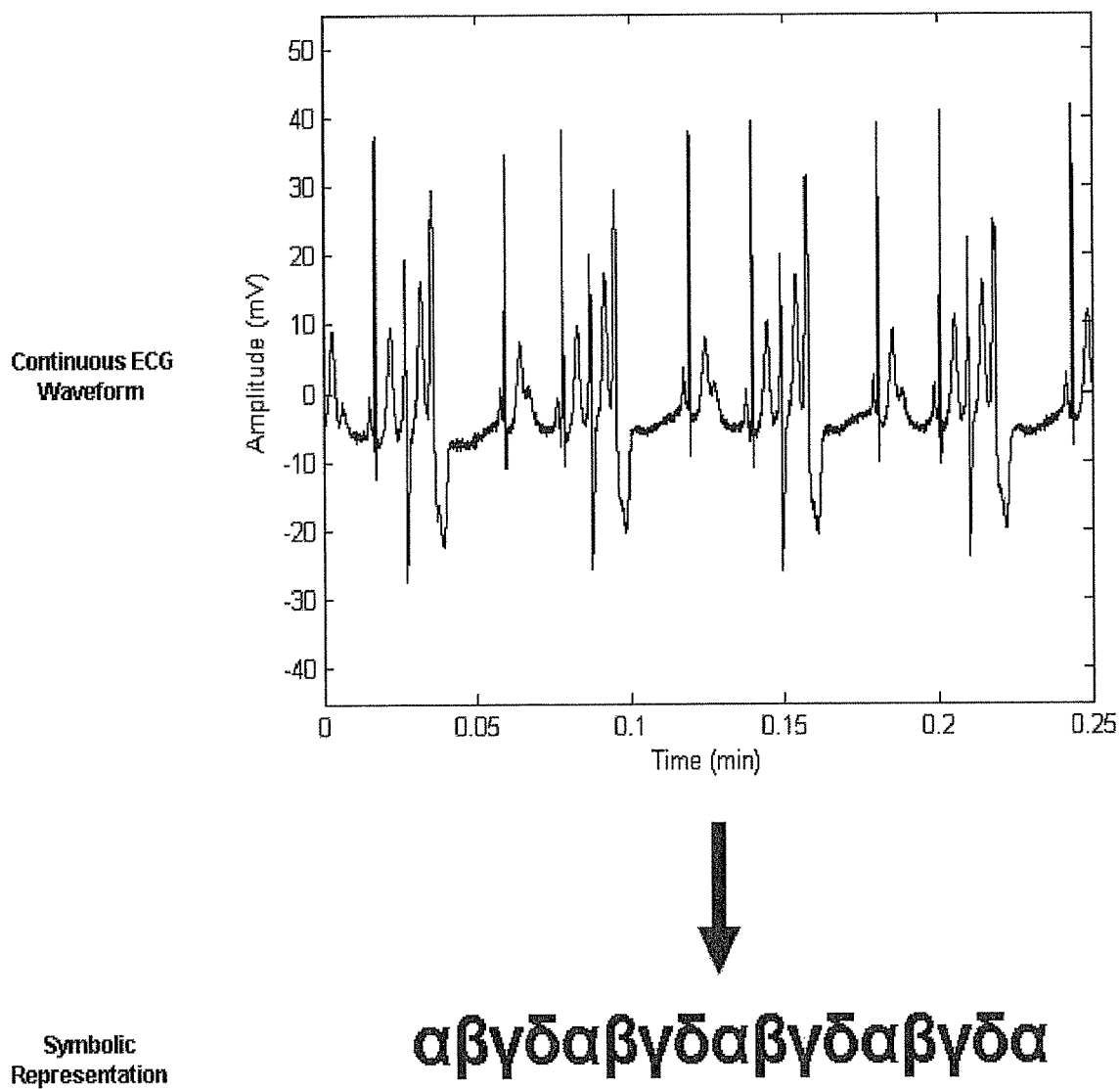
FIG. 2 shows an exemplary transformation of continuous ECG waveform to a string of symbols, in accordance with an illustrative embodiment of the invention. Each of the symbols shown corresponds to a different class of physiological activity.

We use the property of quasi-periodicity in physiological signals to determine appropriate boundaries for segmentation, and then replace each unit with a single representation such as a symbol or value. In the remainder of this application we speak in terms of symbols keeping in mind this is one embodiment of the general term "representation". In doing so, we exploit the underlying repetitive structure and redundancy to obtain a layer of data reduction. The raw physiological data is re-expressed to retain salient differences between units of quasi-periodic activity while abstracting away the common structure. For example, as shown in FIG. 2, raw ECG data can be partitioned at the level of heart beats into different equivalence classes, each of which is assigned a unique alphabetic label for identification. This reduces the data rate from around 4000 bits/second (for a beat lasting one second in a signal sampled at 360 Hz with 11 bit quantization) to n bits/second (where n depends upon the number of bits needed to differentiate between symbols, two for this case).

The data reduction introduced by symbolization reduces the search space for the detection of interesting activity and provides a significant computational advantage over working in the original space of the raw signal. A further advantage of using symbolization is that it implicitly abstracts away some of the time-normalization issues that complicate the use of cross-correlation and other techniques that operate on raw time samples.

Creating Symbolic Representations

To transform continuous waveforms into a string representation that can be mined for patterns more efficiently, we propose segmenting the original signal into intervals and then assigning an alphabetic label to each token. This effectively transforms the original data into a sequence of symbols and maps the problem into the domain of string algorithms.

Figure 3:
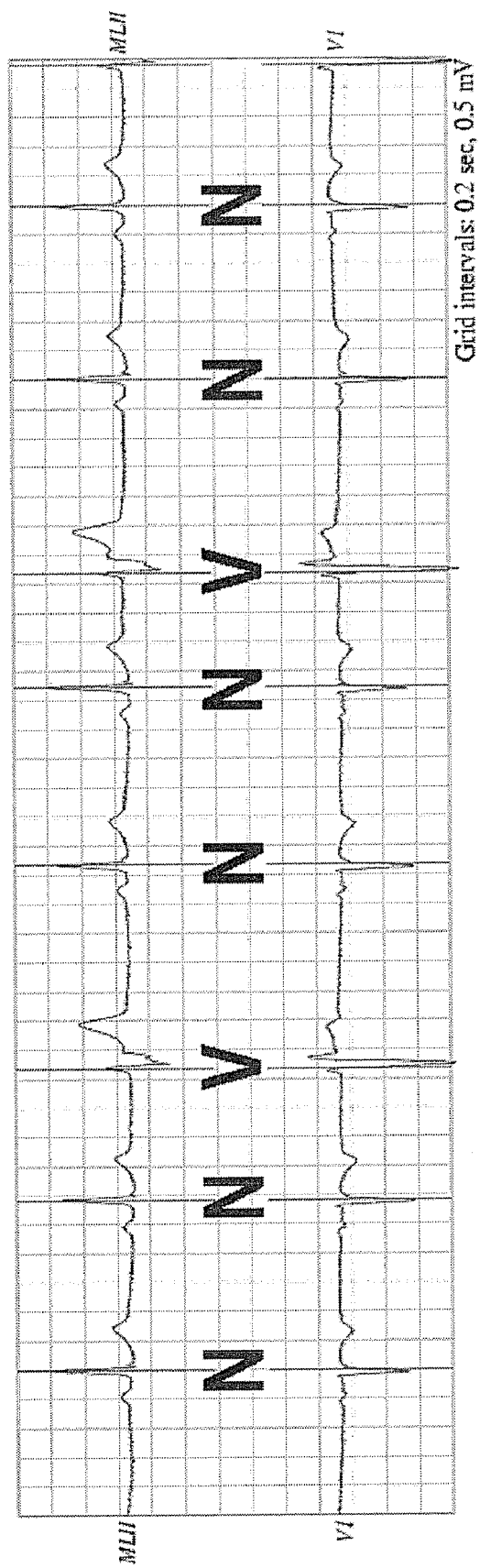
FIG. 3 shows an exemplary symbolization of continuous ECG waveforms using clinical annotations (N=normal, V=premature ventricular contraction), in accordance with an illustrative embodiment of the invention.

The task of assigning labels can be carried out in a number of different ways. One approach is to use clinical information to partition segmented tokens into equivalence classes. This approach provides a set of alphabets that have a fixed meaning in a medical context and can be shared across a population. For example, the ECG signal in FIG. 3 can be decomposed into RR-intervals as shown (each RR-interval corresponds to the period between two successive contractions of the ventricles of the heart, i.e., the period between successive sharp spikes in the raw ECG tracings). Each RR-interval can then be labeled using existing annotations for physiological activity. RR-intervals associated with normal heart beats are labeled N, while those associated with abnormal contractions originating from ventricular regions are labeled V.

Accordingly, patient physiological signals are separated into discrete components, and each variation of that component is assigned a unique representation (e.g., a number or symbol). For example, ECGs from one or more patient are separated into a plurality of discrete waveforms which correspond to individual heart beats. Waveforms corresponding to normal heartbeats are each assigned a unique representation (e.g., the letter N). Waveforms corresponding to abnormal contractions originating from ventricular regions are each assigned a different representation (e.g., the letter V). Further classes of abnormal heart beats are each assigned their own unique symbols. To accommodate for minor variations in individual waveforms, all N waveforms are grouped together and a characteristic N (i.e., normal) waveform is extrapolated therefrom. Characteristic waveforms are also extrapolated for each type of abnormal heartbeat. The characteristic waveforms are then used to evaluate heartbeats in the ECGs of new patients.

The characteristic waveform can be a prototype (archetype) waveform or a centrotype waveform. The difference between the prototype and the centrotype is as follows—the prototype is a waveform we construct that is the 'average' waveform; the centrotype is the waveform of the average element. For example, if we want the average of the numbers 1, 4, 10, the prototype approach would be to use 1+4+10 divided by 3 (i.e., we compute the average). The centrotype approach would be to say that 4 is the middle element. In some embodiments, the representation is a waveform and the probability of the information class.

The approach of using clinical annotations is restricted to detecting predictive activity that expresses itself in terms of known clinical classes. It does not allow for the isolation of changes at the level of variations within particular classes. This is important because the granularity of later analysis is constrained by the granularity of labeling.

From a knowledge discovery goal, it is appealing to derive the alphabets for symbolization directly from the data itself. Techniques such as those in (Syed, Z., Stultz, C. and Guttag, J. 2007. Clustering and symbolic analysis of cardiovascular signals: discovery and visualization of medically relevant patterns in long-term data using limited prior knowledge. EURASIP Journal on Advances in Signal Processing 2007, Article ID 67938) can be employed to achieve this goal. While the approach of generating a patient-specific symbolic representation is powerful in its ability to capture significant changes across a patient, it poses the problem that the clusters are derived separately for each patient. This restricts comparisons across a population. A possible means for addressing this issue is to use a semi-supervised approach where the symbols derived for each patient are related by a human expert. This allows for the symbols to be dynamically derived based on characteristics inherent in the data itself, and for these symbols to be related and compared across a population.

At present, registering patient-specific symbols in a fully automated manner across a population represents an area of continuing work. The discussion that follows therefore assumes the use of clinical annotations (or of semi-supervised symbols related manually across patients).

Section 3: Physiological Motifs in Symbolic Data

In the setting of computational biology, regulatory motifs correspond to short DNA sequences that regulate gene expression. This notion of a genetic 'switch' that controls activity further downstream is well-suited to our model for prediction. We generalize this idea and choose to model regulatory motifs as sequential triggers that precede abrupt clinical events and are conserved across a population of patients owing to an association with the event.

A recent strategy for regulatory motif discovery that has gained popularity is to make use of comparative genomics. This allows for the discovery of regulatory elements by exploiting their evolutionary conservation across related species. Under this approach, regulatory motif discovery can be viewed computationally as finding sequences that are recurrent is a group of strings, upstream of specified endpoints.

The problem of regulatory motif discovery can be stated more formally in either a combinatorial or probabilistic framework. While the two frameworks both attempt to identify similar preceding subsequences, they may lead to slightly different results and require distinct algorithmic techniques.

Combinatorial: Given a set of sequences $\{s_1, \ldots, s_N\}$ find a subsequence $m_1, \ldots, m_w$ that occurs in all $s_i$ with k or fewer differences.

Probabilistic: Given a set of sequences $\{s_1, \ldots, s_N\}$ find a set of starting positions $\{p_1, \ldots, p_N\}$ in the sequences that lead to the best (as defined below) A×W profile matrix M (where A is the number of alphabets in the data and W is the length of the motif).

For the probabilistic case, the profile matrix is derived from the subsequences of length W immediately following the starting positions $p_1, \ldots, p_N$ in each of $s_1, \ldots, s_N$. These subsequences are lined up and the probability of each of the A alphabets at every one of the W motif positions is estimated. M(x,y) then gives the probability that the motif has character x at position y. The resulting profile matrix can be scored using different criteria with the implicit goal of seeking a non-trivial profile that is strongly conserved at each position and best explains the data. The scoring function most often used is the log-odds likelihood, i.e.:

$$\text{score} = \sum_{i=1}^{N} \sum_{j=1}^{W} \log \left[ \frac{M(s_i(p_i + j - 1), j)}{B(s_i(p_i + j - 1))} \right]$$

Where B gives the background distribution of each alphabet in the data. Effectively, this calculates the log-likelihood of a motif while compensating for trivial occurrences that would be seen in the data merely due to the frequent occurrence of certain symbols.

Data Challenges Associated with Motif Detection in Symbolic

The problem of motif discovery gives rise to a number of issues in the physiological setting. This section discusses the major challenges faced with modeling acute clinical events as physiological motifs.

Symbol Distribution Skews

A complication arising in the context of physiological signals is that of the sparsity of abnormal activity. Periods with interesting events are typically separated by long, variable-sized runs of normal behavior, i.e., the distribution of the symbols is significantly skewed in favor of normal labels. This increases the number of trivial motifs in the data and consequently the running time of the motif discovery algorithms. In addition, for algorithms such as TCM and Gibbs sampling discussed in Section 4, a secondary effect resulting from the presence of long stretches of normal behavior is that the starting locations chosen randomly may often correspond to uninteresting regions of the signal, further increasing time to convergence.

Motif Degeneracy

The issue of degeneracy is frequently encountered in DNA sequences and assumes a critical role for physiological motifs as well. Predictive patterns may be approximately conserved across some patients in a population, while in others, they may be missing altogether. This results from a variety of factors, including differences in the age, gender, clinical history, medications and lifestyle of patients, as well as noise obscuring predictive patterns in some recordings.

The goal of detecting imperfectly conserved activity represents a significant challenge to the task of discovering precursors. Since patterns can vary, the process of determining whether a pattern appears in a patient is required to explore a larger search space, spanning all possible variations. Similarly, the fact that some patients may have the predictive activity obscured due to noise requires recognizing these cases and preventing motif discovery algorithms from forcibly incorporating this data in the search process.

Section 4. Computational Biology Algorithms for Motif Discovery

In this section, we review three popular algorithms for finding regulatory motifs using comparative genomics; the Two Component Mixture (TCM) algorithm using expectation-maximization, Gibbs sampling, and Consensus. TCM and Gibbs sampling attempt to solve the probabilistic formulation of motif discovery, while Consensus focuses on the combinatorial problem.

Two Component Mixture (TCM)

TCM is an enhancement to the basic EM algorithm (Bailey, T., and Eklan, C., 1995. The value of prior knowledge in discovery motifs with MEME. In Proceedings of the International Conference on Intelligence Systems in Molecular Biology. Cambridge, UK. 21-29), which essentially reduces the search into two smaller, decoupled problems. The first (i.e., the M-step) involves constructing the profile for a motif given a set of fuzzy starting positions $p_1, \ldots, p_N$ in the input sequences (the M-step). The second (i.e., the E-step) then uses this matrix profile representation to score all possible starting positions in every sequence and update the initial $p_1, \ldots, p_N$.

The overall TCM algorithm operates in the following manner:

---
TCM($\{s_1,\ldots,s_N\}$, W):
1. Set random initial values for profile matrix M
2. Do
    i. E-step to update starting positions
    ii. M-step to update profile matrix
Until the change in the score of M is less than some threshold $\epsilon$

---

The M-step of TCM estimates the profile matrix using the probability $Z_{ij}$ that the motif starts in sequence i at position j. As a first step, the values $n_{c,k}$ are estimated, which indicate how often the character c occurs at position k in the motif $$n_{c,k} = \begin{cases} \sum_i \sum_{j|s_{i,j}=c} Z_{ij} & k > 0 \\ n_c - \sum_{j=1}^{W} n_{c,j} & k = 0 \end{cases}$$

k=0 represents the case where character c occurs in the sequence outside the motif while $n_c$ gives the total number of times c occurs in the data. Using these values, we can obtain a profile matrix M as follows:

$$M_{c,k} = \frac{n_{c,k} + d_{c,k}}{\sum_a (n_{a,k} + d_{a,k})}$$

where $d_{c,k}$ is the pseudocount for character c. When estimating the frequency of a rare event by counting how often it occurs in a finite sample, there is a risk that the count will be zero even though the probability of the event occurring is not zero. Using pseudo count circumvents this potential problem.

In addition to computing the profile matrix during the M-step, TCM also calculates a prior probability that a motif might start arbitrarily at any position in the data. This is denoted by $\lambda$ and is obtained by taking the average of $Z_{ij}$ across all sequences and positions.

TCM primarily differs from other EM approaches to motif discovery in its E-step. For every sequence $s_1$ in the dataset TCM assigns a likelihood $L_{ij}$ to the W-mer starting at each position j:

$$L_{ij}(1) = Pr(s_{ij} | Z_{ij} = 1, M, b) = \prod_{k=j}^{j+W-1} M_{k-j+1,c_k}$$

where $s_{ij}$ is the W-mer in sequence i starting at position j. And:

$$L_{ij}(0) = Pr(s_{ij} | Z_{ij} = 0, M, b) = \prod_{k=j}^{j+W-1} b_{c_k}$$

Where b gives the background probability for each character in the dataset. For iteration t of TCM, the values of $Z_{ij}$ can then be estimated using:

$$Z_{ij}^{(t)} = \frac{L_{ij}^{(t)}(1)\lambda^{(t)}}{L_{ij}^{(t)}(0)[1-\lambda^{(t)}] + L_{ij}^{(t)}(1)\lambda^{(t)}}$$

where $\lambda^{(t)}$ is the probability that a motif might start arbitrarily at any position in the data, as estimated in iteration t.

Gibbs Sampling

Gibbs sampling (Gert, T., Marchal, K., Lescot, M., Rombauts, S., De Moor, B., Rouze, P., and Moreau Y. 2002. A Gibbs sampling method to detect overrepresented motifs in the upstream regions of coexpressed genes. Journal of Computational Biology 9, 447-464) can be viewed as a stochastic analogue of EM for finding regulatory motifs and is less susceptible to local minima than EM. It is also much faster and uses less memory in practice. This is because unlike EM, the Gibbs sampling approach keeps track only of the starting locations $p_1, \ldots, p_N$ of the motif in each sequence and does not maintain a distribution over all possible starting positions for the motif (i.e., the $Z_{ij}$ in TCM representing fuzzy starting positions are replaced by hard $p_1, \ldots, p_N$)

The Gibbs sampling algorithm for motif discovery can then be written as:

---
GIBBS($\{s_1,\ldots,s_N\}$, W):
1. Set random initial values for p
2. Do
    i. Select sequence $s_i$ at random
    ii. Estimate M from set $\{s_1,\ldots,s_N\}-s_i$
    iii. Use M to score all starts in $s_i$
    iv. Pick start $p_i$ with probability proportional to its score
Until the change in the score of M is less than some threshold $\epsilon$

---

Gibbs sampling is less dependent on the initial parameters than TCM and therefore more versatile. However, it is dependent on all sequences having the motif. This is an inefficiency we address in our work.

Consensus

Consensus (Gert, T., Marchal, K., Lescot, M., Rombauts, S., De Moor, B., Rouze, P., and Moreau Y. 2002. A Gibbs sampling method to detect overrepresented motifs in the upstream regions of coexpressed genes. Journal of Computational Biology 9, 447-464) is a greedy motif clustering algorithm that picks out two sequences at random, finds the most conserved pairs amongst them and then iterates over all the remaining sequences adding the W-mers that match best to the results of the previous iteration at every stage.

The Consensus algorithm is as follows:

```
CONSENSUS({s₁,...,s_N}, W):
    1.  Pick sequences s_i and s_j at random
    2.  Find most similar W-mers in s_i and s_j
    3.  For each unprocessed sequence s_k
        i.  Expand solution set with W-mers from s_k that match
            best with previous ones
```

Section 5. Data Transformations and Subset-Based Techniques
Active Regions

The issue of skewed symbol distributions can be addressed by removing long stretches of activity that are known to be uninteresting. By definition, a predictive motif is associated with an acute clinical event and must be associated with abnormal activity. As a result, trivial motifs comprising normal activity can be trimmed away to reduce the running time associated with the motif-discovery algorithms. For example, given the hypothetical below sequence (with N corresponding to normal beats):

VJVJJNNNNNNNNNNNVNVNBBr

A possible reduction of this data would be:

VJVJJN+VN+VN+BBr

This technique is associated with a significant loss of information. Specifically, the search for motifs proceeds in the transformed space, and the N+regular expression may occur in motifs without a consistent meaning (i.e., it may be arbitrarily long in some patients). The more general issue here is that conservation of a pattern in the transformed space does not imply conservation in the original signals.

To avoid this issue, we identify regions of abnormal activity, i.e., active regions, by splicing out trivial periods in the signal. Given a motif length W, this involves iterating over the data and removing all normal symbols that would occur only in trivial motifs. This approach preserves the temporal structure of abnormal stretches of the signal, ensuring that the motifs correspond to patterns that are conserved in all of the original signals. For example, using this approach for a motif of length 3, the original example pattern above would map to:

VJVJJNNVNVNBBr using Gibbs² and Seeded Consensus

The Gibbs sampling algorithm in Section 4 assumes that a motif is present in all sequences. To deal with the issue of degeneracy, where noise may obscure the predictive pattern completely for some patients, we propose a new algorithm that provides a layer of robustness while dealing with a population where activity may be altogether absent in some of the observed examples. This is achieved by adding a second layer of Gibbs sampling to the original algorithm, leading to the Gibbs² algorithm presented here.

The Gibbs² algorithm operates at any time on a working subset $V = \{v_1, \ldots, v_c\}$ of the original sequences $\{s_1, \ldots, s_N\}$. Sequences are dynamically swapped into and out of this set with the goal of replacing poor matches with potentially better options. The underlying goal is to arrive at a cluster of sequences that share a strongly conserved motif.

The initial subset of sequences is chosen at random, and at each iteration, a single sequence $v_i$ in the working set is scored using the profile generated from $V - v_i$. With some probability $v_i$ is swapped out and replaced by one of the sequences outside the working set. The probability of being swapped out varies inversely with the maximum score seen for the sequence at any position, i.e., the score at the position that corresponds most strongly to the profile matrix:

$$\log[\Pr(\text{swap})] \propto -\max_j[\text{score}(v_i(j))]$$

The proportionality factor depends on the length of the motifs being searched for.

The intuition behind the Gibbs² algorithm is that if a sequence scores high for a motif, it matches quite well with other sequences used to derive the profile and is retained with a higher probability. Conversely, if a sequence does not score highly, it matches poorly with the remaining sequences in the working set used to derive the profile.

Ideally, the sequence swapped out should be replaced by one that scores highest on the profile matrix being used. This approach is computationally intensive since all outstanding sequences need to be scored before the optimal one can be chosen. To avoid this, once a sequence is swapped out, it is replaced by any of the sequences outside the working set at random. This avoids the need to score all previously excluded sequences to find the one with the best match. Furthermore, after each swap, further swapping is temporarily disabled to allow the new sequence to be absorbed and contribute to the profile matrix.

The Gibbs² algorithm can be written as follows (with C denoting the size of the working set and K representing the number of iterations swapping is disabled after a sequence is replaced from one outside the working set):

```
GIBBS({s₁,...,s_N}, W, C, K):
    1.  Choose C sequences at random from {s₁,...,s_N}
    2.  Set random initial values for p
    3.  Do
        i.    Select sequence v_i at random
        ii.   Estimate M from set V-v_i
        iii.  Use M to score all starts in v_i
        iv.   Swap out v_i with Pr(swap) and replace it with a
              random sequence outside the working set
        v.    If swap occurs
              a.  Disable swapping for K iterations
        vi.   Pick start p_i with probability proportional to its score
        Until the change in the score of M is less than some threshold ε
```

The Gibbs² approach can be used to iteratively partition the data into a set containing a strongly conserved motif and an outstanding set that can be broken into further subsets sharing a common pattern. This allows for the discovery of multiple predictive motifs occurring in subsets of the population.

The use of Gibbs² also allows for the performance of the Consensus algorithm from Section 4 to be improved. Specifically, Consensus can be seeded using a strongly conserved pattern obtained by Gibbs². This reduces the likelihood that Consensus will be affected by a poor choice of the initial two strings.

Section 6. Evaluation
Testing Methodology

We applied our techniques to the Physionet Sudden Cardiac Death Holter Database (SDDB) (Physionet 2000). This database contains several hours of ECG data recorded using Holter monitors from 23 patients who experienced sudden cardiac death. The recordings were obtained in the 1980s in Boston area hospitals and were compiled as part of a later study of ventricular arrhythmias. Owing to the retrospective nature of this collection, there are important limitations. Patient information is limited, and sometimes completely unavailable, including drug regimens and dosages. Furthermore, sudden cardiac death may result from a variety of underlying causes and it is likely that among the 23 patients there are multiple groups sharing different regulatory factors. Despite these shortcomings, the SDDB ECG signals represent an interesting dataset since they represent a population sharing a common acute event. In addition, the recordings are sufficiently long (up to 24 hours prior to death in some cases) that it is likely the predictive factors occurred during the recording period. Finally, the signals in SDDB are generally well-annotated, with cardiologists providing labels at the level of each beat, and this yields a source of clinically relevant symbols that can be used to search for motifs.

For the 23 SDDB patients TCM, Gibbs sampling, Gibbs$^2$ and Consensus were used to discover potentially predictive motifs of lengths 4, 10 and 16. Since TCM, Consensus and the variants of the Gibbs sampling algorithms are stochastic in nature, a hundred runs were executed with the strongest motifs being automatically returned as the solution. The scoring function used was the log-likelihood score described in Section 3.

In each case, the endpoint used to signify the acute event associated with death was the occurrence of ventricular fibrillation (VF). This was annotated for all patients and only regions preceding VF were searched for conserved motifs.

For visualization purposes, we used WebLogo (Crooks, G., Hon, G., Chandonia, J. and Brenner, S. 2004. WebLogo: a sequence long generator. Genome Research 14, 1188-1190) to display the motifs returned by our algorithms. This uses the profile matrix to represent motifs as sequence logos, which are graphical representations consisting of stacks of symbols. For each position in the motif, the overall height of the stack indicates how strongly the motif is conserved at that position, while the height of symbols within the stack indicates the relative frequency of each symbol at that position. For example, for the length 10 motif in FIG. 4, the sequence logo shows that the motif is strongly conserved at positions 8 and 10, where the predictive sequence was found to contain normal beats across patients. The motif is also conserved at positions 1, 3 and 5, where ventricular activity was seen for most patients, with some occurrences of normal beats (position 1) and supraventricular beats (positions 3 and 5) as well.

For position j in the motif, the height of symbol i at that location is given by:

$$M(i, j)[2 - H(j)]$$

Where:

$$H(j) = -\sum_k M(k, j)\log_2(M(k, j))$$

For Consensus, where a profile matrix is not explicitly constructed, the best-matching subsequences were used to derive a profile that could be represented using WebLogo. This allowed for results to be consistently visualized, irrespective of the algorithm used to discover motifs.

More information on WebLogo is available from the University of Berkeley, Calif. (e.g., http://weblogo.berkeley.edu).

Data Reduction

The transformations discussed in Section 5 can be evaluated in terms of the data compression realized using these approaches. This allows for an appreciation of the degree to which the data contains long runs of normal activity that can be compacted. The original sequences across the 23 patients contained 1,216,435 symbols in total, each corresponding to a single beat annotated by a skilled cardiologist. Using the notion of active regions and stripping away uninteresting normal motifs reduced the size of the data to 257,479 characters, i.e., a reduction of 78.83%.

TCM, Gibbs Sampling and Consensus

Figure 4:
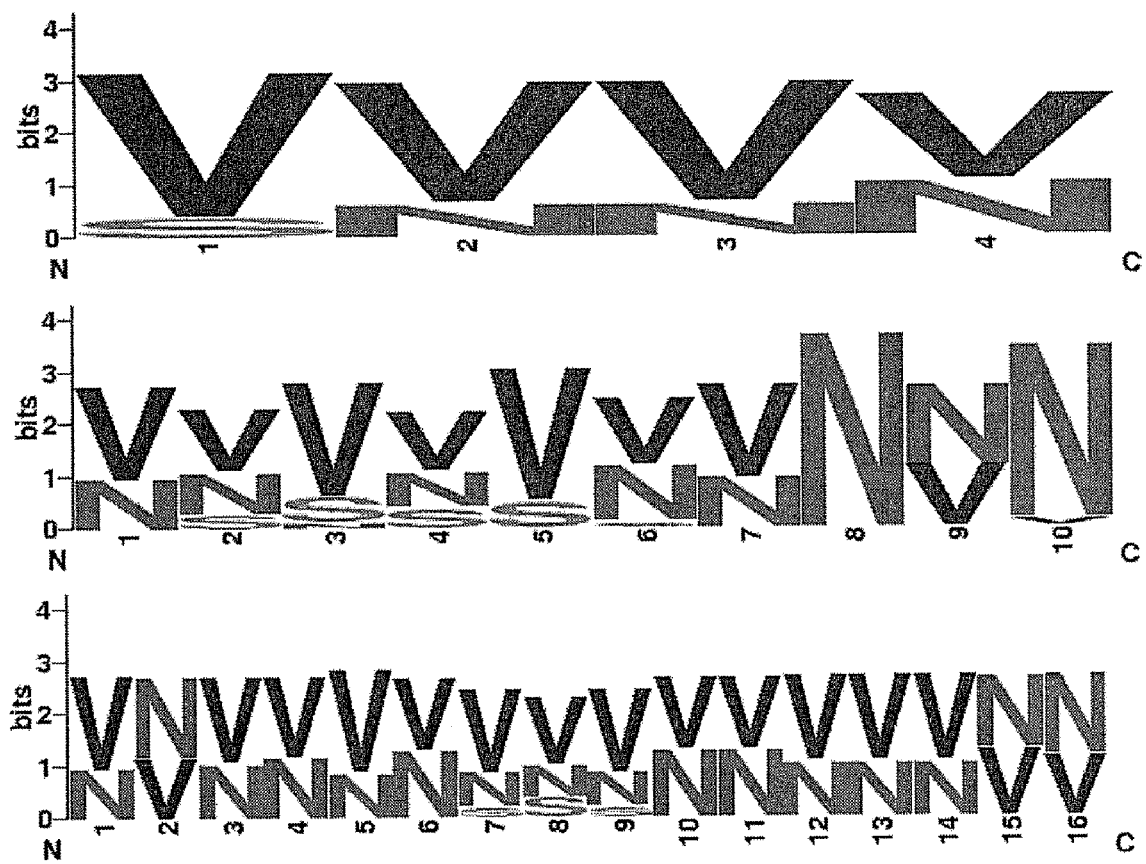
FIG. 4 is a diagram showing motifs of length 4, 10 and 16 found using TCM, in accordance with an illustrative embodiment of the invention.
Figure 5:
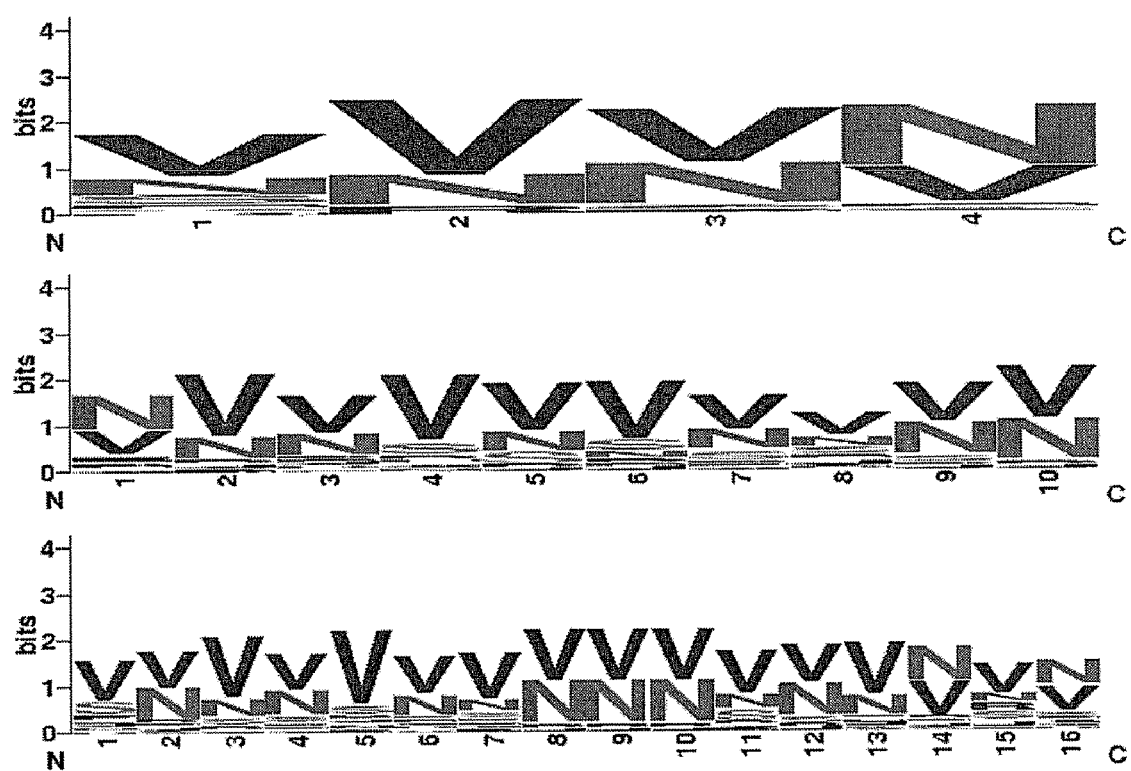
FIG. 5 is a diagram showing motifs of length 4, 10 and 16 found using Gibbs sampling, in accordance with an illustrative embodiment of the invention.
Figure 6:
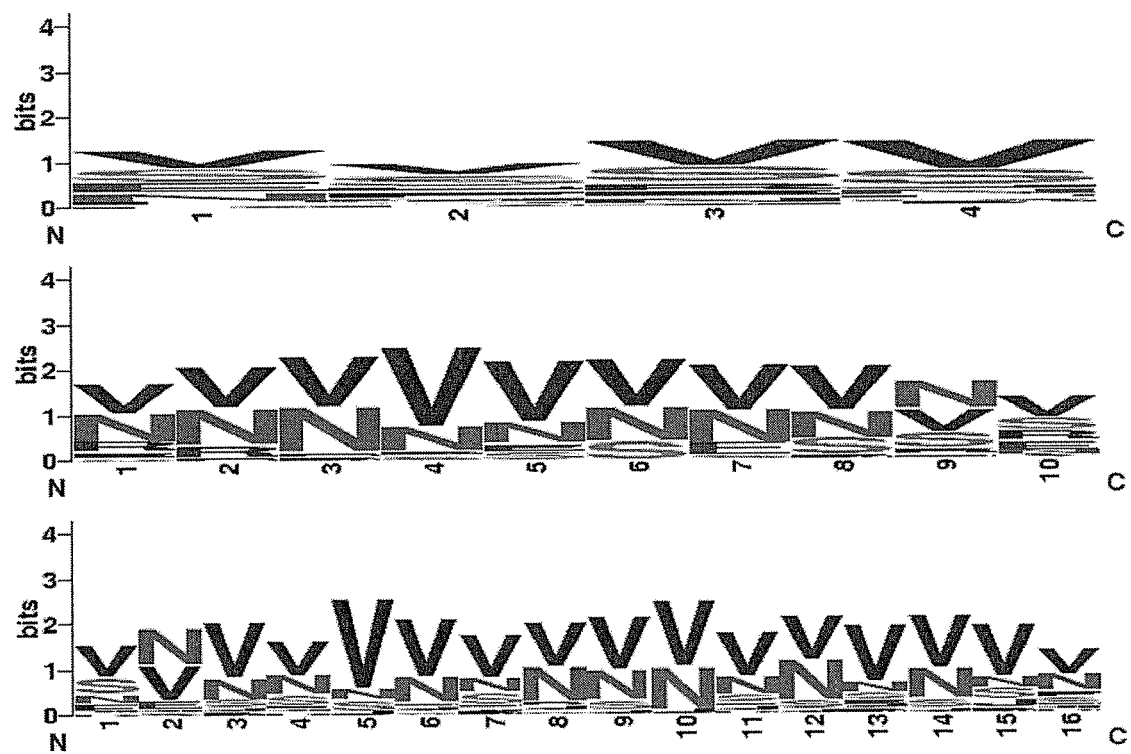
FIG. 6 is a diagram showing motifs of length 4, 10 and 16 found using Consensus, in accordance with an illustrative embodiment of the invention.

FIGS. 4-6 present the results returned by TCM, Gibbs sampling and Consensus as sequence logos. Commonly occurring labels are N=normal, V=premature ventricular contraction, and S=supraventricular premature or ectopic beats.

The motifs discovered by all three algorithms were similar and comprised runs of premature ventricular contractions. For each choice of motif length, TCM returned more strongly conserved motifs than both Gibbs sampling and Consensus. This can be explained by the fact that TCM scores all starting positions in every sequence during each iteration, and is stochastic only in the choice of an initial profile matrix. It employs significantly more computation than either Gibbs sampling or Consensus and is able to find more strongly conserved patterns as a result. On the other hand, the Gibbs sampling algorithm depends on both a random set of initial starting positions and probabilistic choices during each iteration to select a string $s_i$ and a new starting position within that string. Consensus is similar to TCM in that it is stochastic only in its initial choice of sequences to use as seed, but unlike TCM, where a poor initial choice can be corrected during subsequent iterations, in the case of Consensus, the effects of a poor initial choice propagate all the way through.

Although TCM produced the best results in this case, the process of scoring every starting position in each sequence was considerably more time consuming and took an order of magnitude more time than either Gibbs sampling and Consensus.

Gibbs$^2$ and Seeded Consensus

Figure 7:
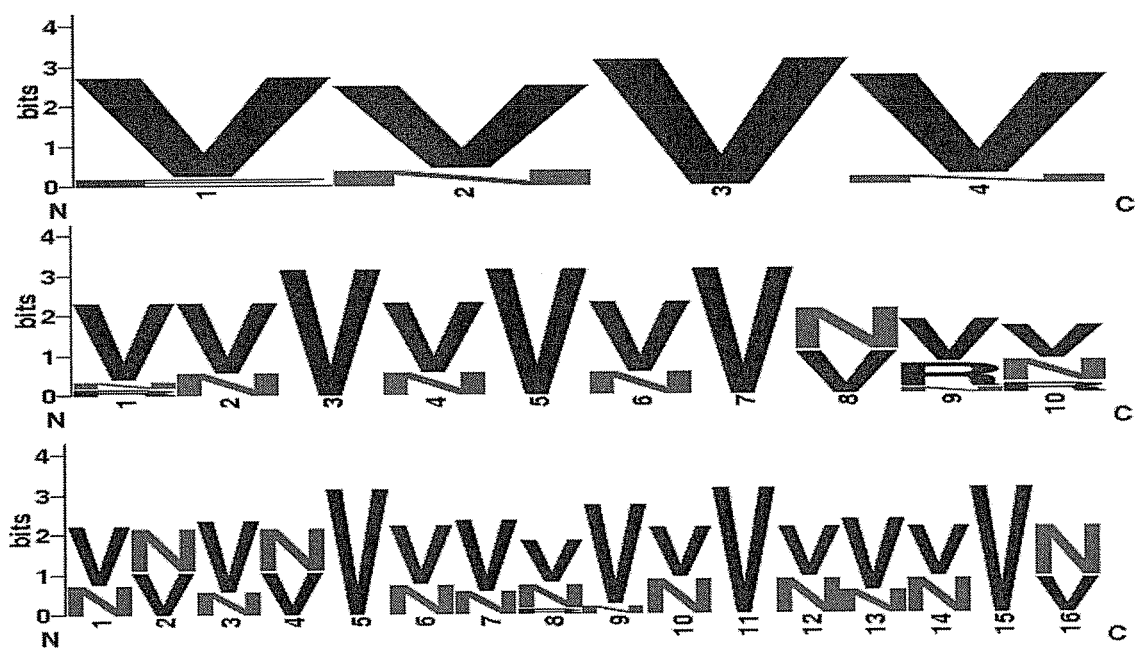
FIG. 7 is a diagram showing motifs of length 4, 10 and 16 found using Gibbs$^2$, in accordance with an illustrative embodiment of the invention.

FIG. 7 shows the motifs discovered by the Gibbs$^2$ algorithm with an initial working set of size 12 chosen at random. In this case, the predictive motif comprised runs of premature ventricular contractions, but was more strongly conserved than the results produce by TCM, Gibbs sampling and Consensus. Specifically, comparing FIGS. 4-7, the stack of symbols in FIG. 7 shows the premature ventricular activity more prominently at positions within the motif.

It is interesting to note that Gibbs$^2$ provides an improvement not only over the original Gibbs sampling algorithm but also the more computationally intensive TCM. The Gibbs$^2$ algorithm has the same basic structure as the original Gibbs sampling technique, but is able to outperform TCM by addressing the issue of subsets of the population exhibiting different regulatory activity.

Figure 8:
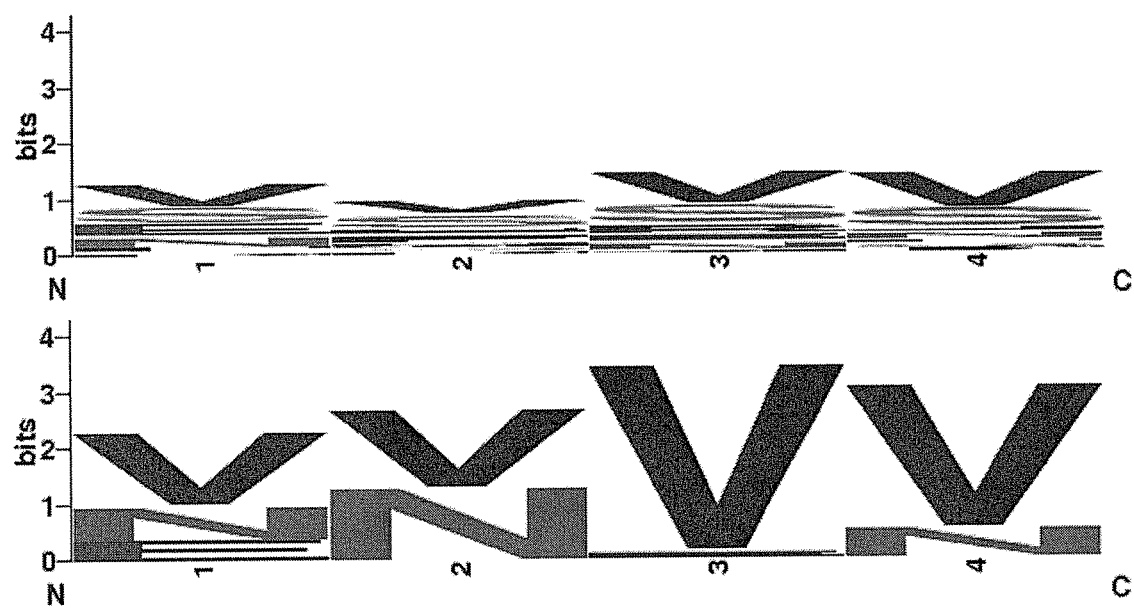
FIG. 8 is a diagram showing motifs of length 4 found using Consensus (top) and Seeded Consensus (bottom), in accordance with an illustrative embodiment of the invention.

FIG. 8 shows the result of using Seeded Consensus to detect motifs of length 4 relative to the original Consensus algorithm. In this case, the Gibbs$^2$ algorithm with a working set of size 5 was used to first find an initial seed for the Consensus algorithm. As can be seen, Seeded Consensus produced considerably better results than the original Consensus algorithm. This effect followed from reducing the chance that a poor initial choice of sequences would propagate and adversely affect the search for motifs.

The motif found using Seeded Consensus in FIG. 8 is not as strongly conserved as the one discovered by Gibbs$^2$ in FIG. 7. This can be explained by the fact that Seeded Consensus uses Gibbs$^2$ to discover an initial seed but otherwise still operates on all the sequences in the data. The degeneracy issue does not therefore get addressed, although Seeded Consensus is able to produce results that are comparable with TCM without the need for intensive computation.

The results of these experiments suggest that subset based techniques using Gibbs$^2$ either to search for motifs directly, or for the purpose of providing seeds that can be fed into the Consensus algorithm, may allow for more strongly conserved motifs to be discovered than through use of TCM, Gibbs sampling and the original Consensus algorithm. Moreover, the improvement provided by the Gibbs$^2$ algorithm proposed in our work is not associated with a significant computational overhead. In addition, the ability to partition the data into groups with homogenous motifs allows for the discovery of more than one predictive pattern, each of which may be associated with the outcome in a different group of patients. We explore this idea in more detail in the next section.

Two-Stage Gibbs$^2$

Figure 9:
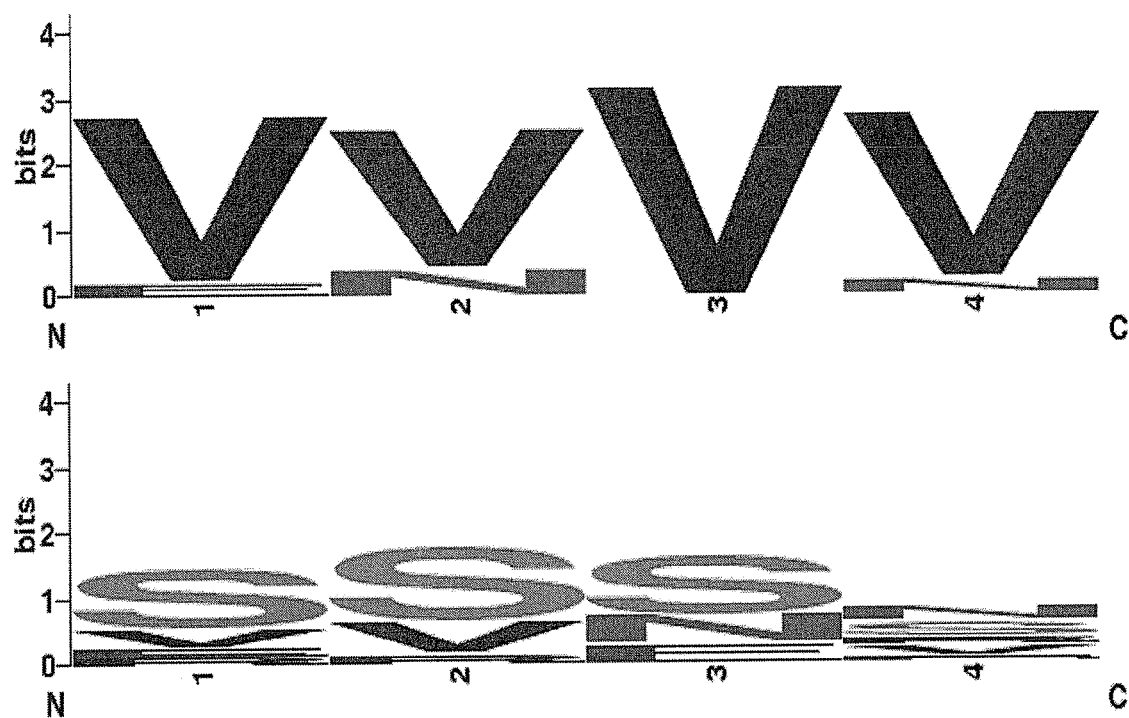
FIG. 9 is a diagram showing two-stage Gibbs$^2$ motifs of length 4, in accordance with an illustrative embodiment of the invention. The top motif comprises a working set of size 12, while the second motif corresponds to those 11 sequences (from a total population of 23) that were not included in the original working set.

For the motif of length 4, the sequences remaining outside the working set at the termination the of Gibbs$^2$ algorithm were searched for a second motif common to this group. FIG. 9 shows the results of this approach.

In this case, a second motif comprising runs of supraventricular premature or ectopic beats was found among this subgroup of the population. Notably, these patients did not show a motif similar to the ones found earlier, i.e., comprising premature ventricular beats, during any of the multiple executions of the motif discovery algorithm. This suggests that the subset of patients left outside the working set by Gibbs$^2$ did not exhibit regulatory activity similar to the ones for whom a premature ventricular motif was discovered. Including these patients in the search for a predictive motif, as would be the case for non-subset-based techniques, would therefore lead to a less informative motif and would obscure the fact that different groups of patients show varied predictive patterns associated with an endpoint.

Motif-Event Delay

Using the motif of length 10 shown in FIG. 7, for each sequence, the time delay between the starting location of the motif, i.e., $p_t$, and VF was calculated for the Gibbs$^2$ algorithm. For one of the 23 patients in the dataset, the motif occurred less than a minute prior to the event itself. In all other cases, the motif discovered preceded the actual event by at least 20 minutes or more. The median motif-event delay was 60 minutes, while the 25% and 75% quartile times were 42 and 179 minutes respectively. The maximum time separation of the motif and the event was 604 minutes.

These results suggest that the motif occurred sufficiently in advance of the endpoint to be considered merely an extension of the final event itself. Furthermore, the fact that the motif may occur at a wide range of times prior to the endpoint reinforces the need to carry out the search for predictive patterns in an automated manner, which is able to relate information across a range of positions within each sequence.

Comparison with Controls

For each patient in the SDDB population, the log-likelihood score was calculated for each starting position in the ECG label sequence. The overall score for the patient was the maximum log-likehood score found. Intuitively, this strategy assigns each patient the risk score associated with the occurrence of the discovered motif of length 10 shown in FIG. 7 at any point during the recording, i.e., if activity similar to the motif associated with sudden death is seen anywhere, the patient is assumed to be at higher risk for the event.

Figure 10:
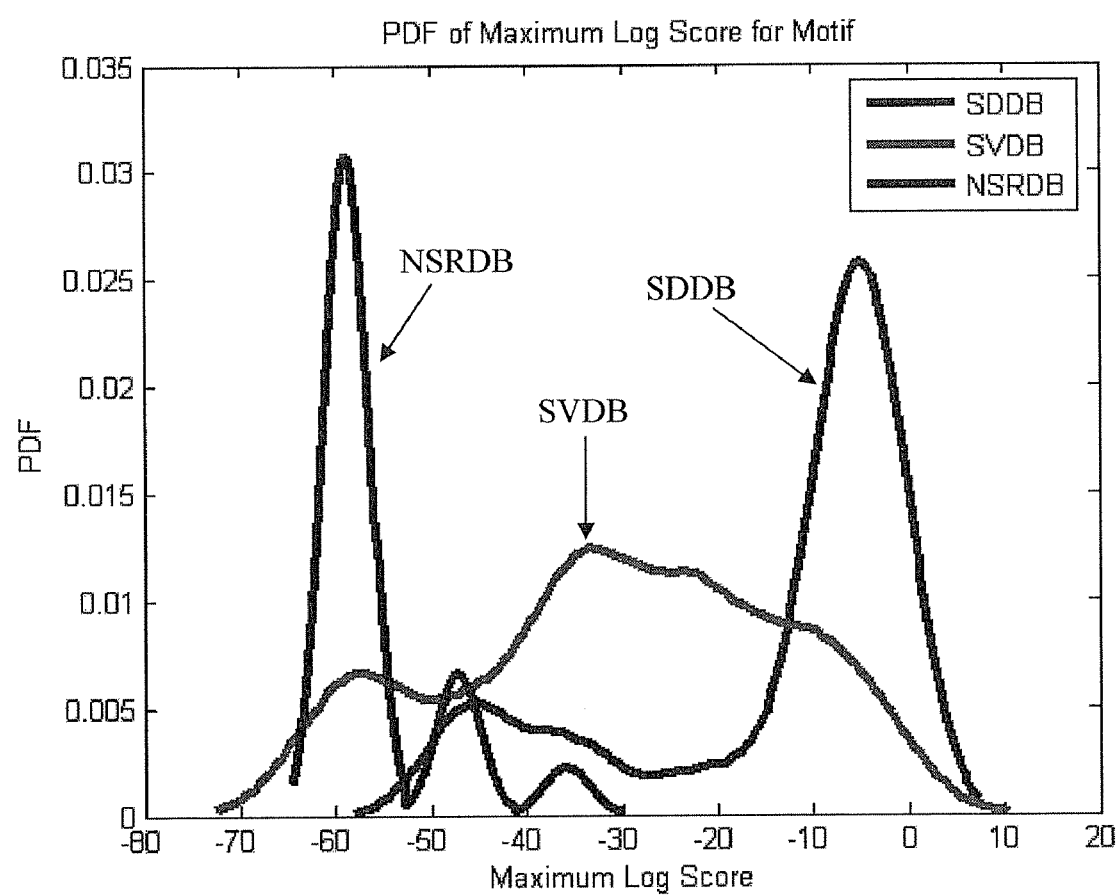
FIG. 10 is a diagram showing motif-matching scores for patients in the Sudden Death Database (SDDB), Supraventricular Arrhythmia Database (SVDB) and Normal Sinus Rhythm Database (NSRDB), in accordance with an illustrative embodiment of the invention. The graph shows the probability distributions estimated using kernel density estimation.

FIG. 10 shows the probability density function that can be estimated from the scores for the SDDB population. A similar strategy was adopted to score patients in two control datasets; the Physionet Normal Sinus Rhythm Database (NSRDB) and the Physionet Supraventricular Arrhythmia Database (SVDB). The decision to use SVDB data in addition to normal individuals was owing to the fact that the SVDB signals contained the same labels as the SDDB data with a higher background frequency of abnormal symbols. This ensured that a difference in scores across populations did not result from an absence of labels, but more so because activity was organized in different forms. Specifically, 1.45% of the beats in the SDDB data were premature ventricular contractions. By comparison, 5.39% of the beats in the SVDB signals and 0.002% of the NSRDB beats fell into the same category. This suggests that if the motifs seen in the SDDB population were random occurrences, then they would be expected to be seen more frequently in the SVDB dataset. With this in mind, the fact that SVDB patients had a higher percentage of premature ventricular activity but still scored lower on the discovered motifs provides further indication that the motif corresponded to activity that was not purely a random occurrence in the sudden death population.

Using a maximum likelihood separator, we were able to use our motif to correctly identify 70% of the patients who suffered sudden cardiac death during 24 hours of recording while classifying none of the normal individuals, and only 8% of the patients from the supraventricular dataset as being at risk. The small number of patients in the dataset, however, does not allow for us to make statistically significant clinical statements about these findings.

Section 7. Related Work

In this section, we review existing knowledge-discovery work to detect potentially predictive activity. A discussion of aspects of our work extending computational biology techniques appears earlier in Sections 3 and 4.

An extensive literature exists in the area of machine learning on the subject of prediction. A common approach is to infer prediction rules from the data of the form:

IF cond$_i$ AND . . . cond$_j$ . . . AND cond$_m$ THEN pred

These rules correspond to a set of conditions associated with a specific outcome. The challenge in this case is to select conditions that are able to distinguish between whether an event occurs or not, but do not overfit available training data. A number of different techniques exist for this purpose, ranging from decision trees to more recent work using evolutionary algorithms.

We supplement this work by finding precursors that exist at a lower level of the data. As an alternative to rules based on the outcomes of a series of diagnostic tests or a sophisticated feature set, we attempt to find interesting patterns by analyzing the specific sequences a system moves through. Such an approach is needed in view of the ever-increasing amounts of data collected in various fields, e.g., medicine, geodesic studies, space and planetary sciences. In many of these cases, well-formulated predictive attributes do not exist. Unsupervised techniques can, however, be used to decompose signals into stationary or periodic tokens. These can then be assigned labels to re-express the original data as a sequence of symbols. Our work allows for the discovery of a specific class of regulatory activity (i.e., occurring as subsequences) in this representation without assuming higher-level features for classification. The analysis of sequential signals is similar to the use of Markov models to study systems. Our work differs from a purely Markovian approach in that we do not attempt to develop a model explaining the data and focus instead on explicitly identifying predictive elements. Furthermore, in many cases, including the sudden death study conducted as part of this project, the regulatory activity may occur well in advance of the event. Developing a Markov model containing sufficient memory and complexity to handle these cases would prove to be challenging in such situations.

A different form of prediction in learning theory is to approach the task in an online manner and consistently refine a hypothesis based on errors and temporal differences. This approach is similar to the inference of prediction rules in that decisions are made on attributes or features and not individual sequences. Our techniques further differ in that they attempt to exploit the availability of batch data and do not address the issue of online learning.

In addition to suggesting methods to discover motifs, we propose subset-based techniques that can isolate subsets of the data that share common predictive motifs. The two-stage Gibbs[2] can find subpopulations sharing different predictive sequences. This is important since the same event may be associated with different causes. We consider the selection of sequences that share regulatory activity as being internal to the problem of motif discovery. Specifically, partitioning the data in advance without information on the specific predictive pattern is difficult, i.e., subsets of the sequences sharing a motif can only be isolated once the motif is known. For this reason, we address the issue of degeneracy and heterogeneous predictive patterns as part of motif discovery and tailor our algorithms to automatically recognize and handle these cases.

Finally, our work is similar to unary classification techniques (Scholkopf, B., Platt, J., Shawe-Taylor, J., Smola, A., and Williamson, R. 2001. Estimating the support of a high-dimensional distribution. Neural Computing 13, 1443-1471) in that the algorithms proposed do not require the presence of both positive and negative examples. Instead, they are geared towards selecting subsequences of labels that can be found across a population in a form unlikely to occur purely by chance. The goal is to better understand similarities that can be analyzed for a predictive relationship with the acute event being considered.

This application focuses mainly on how motif detection was able to identify predictors for sudden cardiac death, i.e., physiological activity in the ECG signal occurring in the hours leading up to sudden death. In additional work, we have focused on the following applications:

1. Using motif detection to predict arrhythmias, myocardial infarction, recurrent ischemia
2. Using motif detection to predict epileptic seizures (in cases where the seizure may be associated with cardiac activity)

Section 8. Measuring Morphologic Entropy

In addition to the techniques described above to find high risk motifs in symbolic sequences, a different kind of distribution that may be associated with adverse outcomes is the entropy of the symbolic sequence (we call this the morphologic entropy).

Once a physiological signal has been symbolized, its morphologic entropy can be defined as:

$$H(x) = -\sum_{c_i \in S} f(c_i) \log(f(c_i))$$

Where $j(c_i)$ is the frequency of symbol $c_i$ in the symbolic representation of the signal.

Section 9. Evaluating Morphologic Entropy

We evaluated morphologic entropy in a preliminary study on fetal ECG signals from five subjects. Inflammatory conditions such as intrauterine infection (chorioamnionitis) during pregnancy are associated with an increased risk of sepsis, cerebral palsy, and death in newborns. Early detection of inflammation may allow for interventions that reduce the risk of adverse newborn outcome. We studied whether morphologic entropy could be used to help with the early detection of inflammation.

Fetal ECG signals were sampled at 1000 Hz with 32 bit quantization and recorded using a fetal scalp electrode placed for a clinical reason following amniotic rupture. The recording of patient data was carried out at the Brigham and Women's Hospital, Boston, Mass. USA, with informed consent obtained from mothers considered at high risk for delivering a baby with fetal injury. Each recording was between 57-200 minutes long with a mean recording duration of 144 minutes. We assessed the quality of each fetal ECG signal using the Physionet Signal Quality Index (SQI) package and by measuring the standard deviation (SD) of the normalized R-wave amplitude. All five recordings were found to be sufficiently high quality (i.e., SQI>90% and SD<0.2887) for further analysis.

For each patient, IL-6, IL-8 and NSE were also measured from cord serum using fully-automated random and enzyme-linked immunosorbent assays. The sensitivity and coefficient of variation (CV) for the assays were 1 pg/ml and <10% for IL-6, 10 pm/ml and <10% for IL-8 and 1 ug/l and <5% for NSE. Abnormal ranges for the biomarkers were chosen from the literature to be >11 for IL-6, >90 for IL-8 and >12.5 for NSE.

Figure 11:
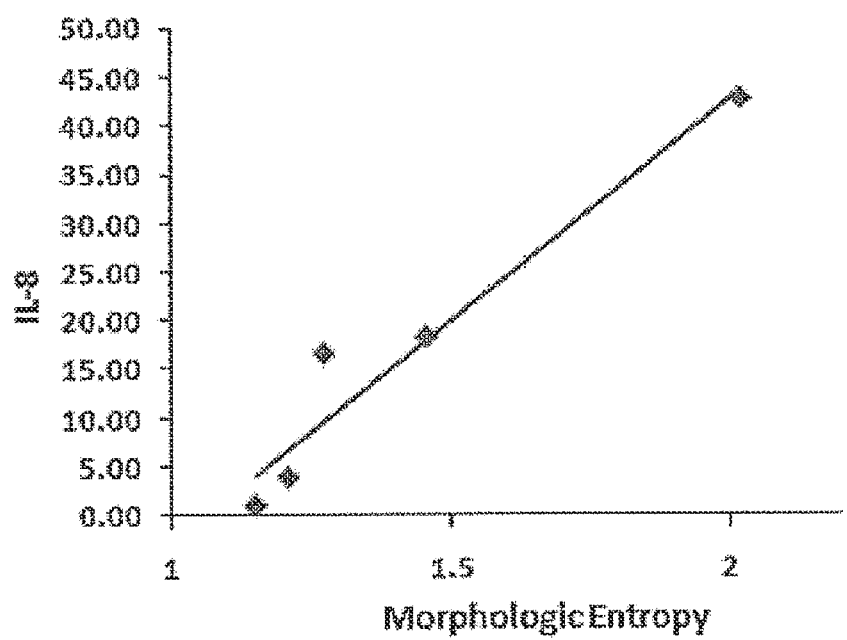
FIG. 11 is a graph showing the relation between morphologic entropy and IL-6 levels in cord blood, in accordance with an illustrative embodiment of the invention. Y=−59.13+ 55.67X; p=0.019; standard error for coefficients=17.38 and 11.93; RMSE=7.68.
Figure 12:
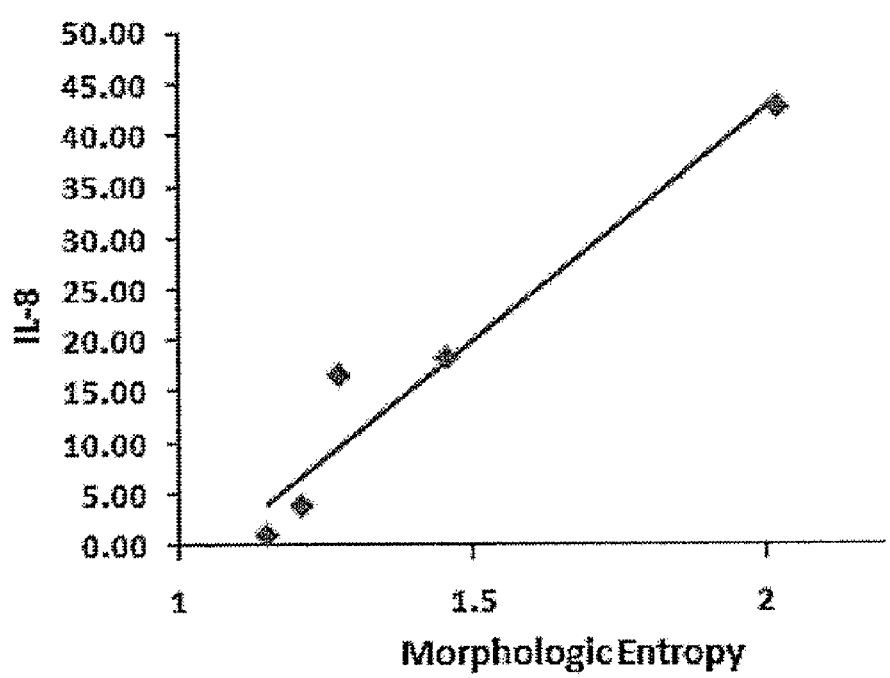
FIG. 12 is a graph showing the relation between morphologic entropy and IL-8 levels in cord blood, in accordance with an illustrative embodiment of the invention. Y=−48.89+ 45.82X; p=0.009; standard error for coefficients=11.01 and 7.56; RMSE.
Figure 13:
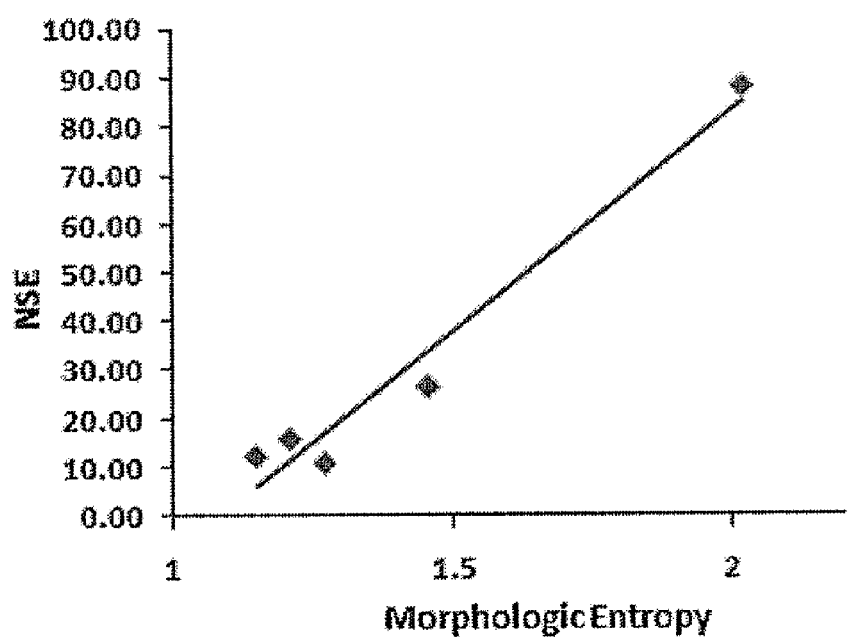
FIG. 13 is a graph showing the relation between morphologic entropy and NSE levels in cord blood, in accordance with an illustrative embodiment of the invention. Y=−97.73+ 90.38X; p=0.005; standard error for coefficients=17.67 and 12.14; RMSE=7.34.

FIGS. 11-13 show the association between morphologic entropy and IL-6, IL-8 and NSE. In each case, we observed a strong linear relation between morphologic entropy and marker levels in cord serum (p<0.05). As the measured IL-6, IL-8 and NSE levels increased, there was an associated increase in the entropy of the fetal ECG morphology.

In addition to the markers of inflammation and neuronal injury, periodic maternal temperature measurements were also recorded for all five subjects. None of the mothers developed a fever during labor, despite the increased IL-6, IL-8 and NSE levels in the cord serum in some of the cases. Furthermore, in the period of hospitalization post-labor, fever was observed in only one of the five mothers. The cord levels of the different markers for this case were IL-6=4.98 pg/ml, IL-8=3.81 pg/ml and NSE=15.85 ug/l, i.e., the mother did not represent one of the cases with the highest inflammatory or brain injury markers in the cord labs. This data suggests that while morphologic entropy of the fetal ECG is strongly associated with IL-6, IL-8 and NSE levels in the cord blood, the absence of fever in the mother is a poor predictor of the lack of inflammation or neuronal injury.

We also evaluated different metrics based on heart rate variability for association with IL-6, IL-8 and NSE. We measured the standard deviation of normal-to-normal intervals (SDNN), standard deviation of sequential five minute normal-to-normal means (SDANN), mean of the standard deviation of sequential five minute normal-to-normal intervals (ASDNN), root mean square successive differences (rMSSD), heart rate variability index (HRVI), percent of normal-to-normal interval increments greater than 50 ms (pNN50) and the ratio of low frequency power to the high frequency power (LF/HF) metrics proposed by the Task Force of the European Society of Cardiology and the North American Society of Pacing and Electrophysiology (TFESC-NASPE) for each patient. Each metric was implemented exactly as proposed in the TFESCNASPE report. Tables 1 and 2 present the HRV metrics computed for each subject and the measured levels of the markers in cord blood. None of the HRV metrics showed a statistically significant linear relation (i.e., p<0.05) with IL-6, IL-8 or NSE. These data suggest that in this study population, HRV metrics were a poor indicator of inflammation or brain injury to the fetus.

TABLE 1

HRV metrics for subjects. Mean heart rate (Mean HR) and the standard deviation of the heart rate (STD HR) are also provided for each subject.

| ID | SDNN | SDANN | ASDNN | HRVI | PNN50 | RMSSD | LF/HF | MEAN HR | STD HR |
|----|------|-------|-------|------|-------|-------|-------|---------|--------|
| 1  | 54   | 30    | 39    | 16   | 0.25  | 26    | 1.64  | 123     | 13.9   |
| 2  | 65   | 32    | 49    | 4    | 0.08  | 21    | 2.24  | 101     | 16.5   |
| 3  | 50   | 28    | 42    | 9    | 0.13  | 22    | 2.36  | 114     | 12.8   |
| 4  | 23   | 14    | 18    | 6    | 0.02  | 9     | 2.79  | 104     | 5.7    |
| 5  | 40   | 19    | 32    | 7    | 0.16  | 20    | 2.98  | 107     | 10.9   |

TABLE 2

Cord blood markers for subjects

| ID | IL-6 | IL-8 | NSE |
|----|------|------|-----|
| 1  | 34   | 18   | 27  |
| 2  | 12   | 17   | 11  |
| 3  | 49   | 43   | 88  |
| 4  | 5    | 4    | 16  |
| 5  | 1    | 1    | 12  |

Section 10. Summary and Conclusions

In this invention, we propose a framework for discovering potentially predictive activity preceding acute events. We generalize the notion of regulatory motifs from computational biology and adapt existing algorithms to operate robustly and efficiently on a broad set of data. We develop and evaluate this work in the context of physiological signals, detailing the challenges associated with fitting a motif-detection model to signals besides DNA. We also describe the performance of subset-based techniques to discover activity associated with sudden cardiac death, comparing discovered patterns against control populations comprising normal individuals and those with supraventricular arrhythmias.

Our work represents a fully-automated approach for discovering a specific class of possible precursors, i.e., patterns that are sequential in that a given ordering of different classes is associated with an end result. We impose no restrictions on the patterns to be discovered, and our tools are able to identify sequences of arbitrary complexity that occur in a possibly degenerate form across a population sharing an event.

A central requirement for the techniques described in this application is that the data being mined is symbolic. In the context of physiological signals, this requires transforming continuous waveforms into alphabetical sequences. Creating a set of labels that can be applied to the data can be achieved in a number of different ways. In the work described here, we use clinical labels that have a fixed meaning and can be applied across patients. It is possible that potentially predictive activity may occur at a more subtle level, where differences within clinical classes are important. For this reason, an important future direction of this research is to extend approaches to annotate signals in a patient-specific, data-derived manner to achieve symbolization.

Finally, it is important to stress that although our initial results on detecting a predictive pattern associated with sudden cardiac death appear promising, the small number of patients in the dataset and limited patient histories means that further investigation on a larger set of ECG signals is necessary.

In addition to this, we also describe how a mechanism for measuring the entropy of the symbolic sequences (i.e., morphologic entropy) can be used as a pattern to identify high risk patients. We showed how high morphologic entropy is associated with inflammatory conditions such as intrauterine infection (chorioamnionitis) during pregnancy are associated with an increased risk of sepsis, cerebral palsy, and death in newborns.

In this application the invention is discussed generally in terms of a method for detecting a predictive pattern associated with various physiological states. The invention can be implemented as a physiological (e.g., electrophysiological) monitor (e.g., ECG) in communication with, for example, a general purpose computer. The physiological signal data is received and stored in a data storage device for subsequent analysis by the program modules of the computer. Individual program modules include but not limited to: dividing the signal data into a plurality of time portions; assigning a representation to each time portion; compressing or removing normal physiological signals; and assigning a significant event to a predictive substantially conserved sequence of representations or symbols. It is contemplated that in another embodiment such program modules may in fact be incorporated into the ECG monitor itself. The data storage device can be in bidirectional communication with the computer such that the computer can retrieve physiological data from the data storage device and the computer can save physiological data (e.g., new patient data) and analytical results to the data storage device. The computer optionally can be in communication with a display for displaying physiological data, time portions, risk profiles, risk scores, representations, symbols, numbers, waveforms, clustering and other features as described herein.

In addition, while the invention is discussed in detail with respect to predicting sudden cardiac death, the invention is equally useful for predicting and/or detecting a wide variety of afflictions. For example, the invention can be used to detect inflammation or neuronal injury in fetuses (i.e., conditions that may lead to, for example, cerebral palsy) to noninvasively predict when C-sections may be helpful or, conversely, when the risk of cerebral palsy is low and C-section might be unnecessary.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

The invention claimed is:

1. A method of detecting patterns in a collection of raw physiological time-series information comprising the steps of: recording raw physiological time-series information from a patient using a device; segmenting the raw physiological information from the device into a plurality of components using a processor; grouping the components into a plurality of time-series information classes using a processor; assigning a symbolic representation to each information class using a processor; searching, using a processor, for patterns of these symbolic representations in a database; and determining the physiological condition associated with the symbolic representation using a processor.

2. The method of claim 1 wherein the pattern may be a sequence of representations.

3. The method of claim 2 wherein the sequence of representations occurs more often than expected given the distribution of symbolic representations.

4. The method of claim 2 wherein the pattern is a sequence of representations that occur more often than expected in patients who have an event.

5. The method of claim 2 wherein the pattern is a sequence of representations that occur more often than expected in patients who have an event relative to patients who do not have an event.

6. The method of claim 1 wherein the pattern may be the entropy of the representations.

7. The method of claim 1 further comprising the step of compressing multiple equivalent time portions that contain normal raw physiological time-series information.

8. The method of claim 1 further comprising the step of removing multiple equivalent time portions that contain normal raw physiological time-series information.

9. The method of claim 1 further comprising the step of assigning a significant event to a predictive conserved sequence of symbolic representations.

10. The method of claim 1 wherein the raw physiological time-series information is an ECG and the equivalent time portion is a heartbeat.

11. An apparatus for detecting patterns in a physiological signal comprising: a module for dividing the physiological signal into a plurality of equivalent time portions; and a module for assigning a symbol to each portion of the plurality of equivalent time portions.

12. The apparatus of claim 11 further comprising a module for recording the physiological signal from a patient.

13. The apparatus of claim 11 further comprising a module for removing multiple equivalent time portions that comprise normal physiological signals.

14. The apparatus of claim 11 further comprising a module for compressing multiple equivalent time portions that comprise normal physiological signals.

15. The apparatus of claim 11 further comprising a module for assigning a significant event to a predictive substantially conserved sequence of symbols.

16. The apparatus of claim 11 wherein the module for recording a physiological signal is an ECG and the equivalent time portion is a heartbeat.

17. A method of detecting patterns in raw time-series of physiological information comprising the steps of: recording on a device the raw time-series of physiological information from a patient; dividing the raw time-series of physiological information into a plurality of equivalent time portions using a processor; assigning a symbolic representation to each portion of the plurality of equivalent time portions using a processor; and searching a database of symbolic representations to determine the physiological condition associated with the symbolic representation.

18. The method of claim 17 further comprising assigning a significant event to a predictive conserved sequence of symbolic representations.

19. A method of finding a consensus motif of length W in a set of physiological sequences $S=\{S_1, \ldots, S_n\}$ utilizing a working set $V=\{v_i, \ldots, v_c\}$ comprising the steps of: a. obtaining the physiological data set (S); b. estimating a profile matrix M for the working set $\{V-v_i\}$ wherein V is an initial subset of set S and $v_i$ member of the working set V; c. calculating a probability that a member $v_i$ of the working set V will be swapped out; d. if the probability that $v_i$ is swapped out exceeds a predetermined probability $p_{pd}$, then swap out $v_i$ for $v_{inew}$; and disable swap of $v_{inew}$ for k iterations; e. select new initial staring position $p_{new}$; and f. repeat until M is less than some threshold $\epsilon$.

20. The method of claim 19 further comprising the steps of 1. choosing an initial subset V of set S; 2. selecting an initial starting position p; and 3. selecting a member $v_i$ of the working set V, prior to estimating the profile matrix M.

21. The method of claim 19 wherein initial starting position is selected randomly.

22. The method of claim 19 wherein the probability that $v_i$ is swapped out is a probability function.

23. The method of claim 22 wherein the probability function is a function of maximum score.

24. The method of claim 19 wherein the selecting of a new initial staring position $p_{new}$ is random.

25. A method of finding a consensus motif of length W in a set of physiological data sequences $S=\{S_i, \ldots, S_n\}$ utilizing a working set $V=\{v_i, \ldots, v_c\}$ comprising the steps of: a. obtaining physiological data set S; b. choosing an initial subset V of set S; c. selecting an initial starting position p; d. selecting a member $v_i$ of the working set V; e. estimating a profile matrix M for the working set $\{V-v_i\}$; f. calculating a probability that a member $v_i$ of the working set V will be swapped out; g. if the probability that $v_i$ is swapped out exceeds a predetermined probability $p_{pd}$, then swap out $v_i$ for $v_{inew}$; and disable swap of $v_{inew}$ for k iterations; h. select new initial staring position $p_{new}$; and i. repeat steps c-g until M is less than some threshold $\epsilon$.

* * * * *